United States Patent [19]
Pratt
[11] 3,941,808
[45] Mar. 2, 1976

[54] PRODUCT

[75] Inventor: Richard J. Pratt, Flossmoor, Ill.
[73] Assignee: Atlantic Richfield Company, Los Angeles, Calif.

[22] Filed: June 29, 1970
[21] Appl. No.: 60,171

Related U.S. Application Data
[62] Division of Ser. No. 795,070, Jan. 29, 1969, Pat. No. 3,575,861.

[52] U.S. Cl. ........ 260/326.26; 252/51.5 A
[51] Int. Cl.$^2$ ........ C07D 207/20
[58] Field of Search ........ 260/326.3, 326.26

[56] References Cited
UNITED STATES PATENTS 3,206,425 9/1965 Muller et al. ........ 260/29.6

*Primary Examiner*—Joseph A. Narcavage
*Attorney, Agent, or Firm*—John C. Martin, Jr.

[57] ABSTRACT

The present invention provides oil-soluble, polymeric surface-active agents which are polyimide-amine salts of styrene-maleic anhydride copolymers having pendant tertiary amine groups containing a salt-forming tertiary nitrogen atom neutralized to the extent of at least about 75 percent with mono-carboxylic acids for instance having an aliphatic chain of at least about 8 carbon atoms. The salts of this invention exhibit the property of lowering the surface tension at oil-water interfaces. The polyimide-amine salts can also contain mixed imides resulting from the reaction of dialkylaminoalkylamines and monoalkyl amines or mixed imide-amides resulting from the reaction of dialkylaminoalkylamines and dialkylamines. This invention also provides oil compositions containing mineral oil and the cil-soluble, polymeric surface-active polyimide-amine salts, with or without water. These compositions are useful, for instance, as hydraulic fluids, jet fuels, electrolyte-containing oils, anti-wear lubricating oils, diesel fuels, and gasolines.

9 Claims, No Drawings

PRODUCT

This is a divisional of application Ser. No. 795,070, filed Jan. 29, 1969, now U.S. Pat. No. 3,575,861.

This invention relates to highly surface-active, oil-soluble agents made from styrene-maleic anhydride copolymers, and to normally liquid mineral oil compositions containing these agents. More particularly, this invention is concerned with salts prepared by converting the anhydride rings of styrene-maleic anhydride copolymers to polyimides containing pendant tertiary amine groups. These pendant tertiary amine groups are neutralized with monocarboxylic acids to form salts that are oil-soluble and exhibit the property of lowering the surface tension at oil-water interfaces, as well as anti-wear characteristics.

It is known to those familiar with the art that surface-active agents in general are derived from balancing hydrophobic and hydrophilic properties. A molecule to be surface-active should contain both types of properties, and this occurs most commonly where a hydrocarbon residue terminates with an ionic or water-soluble fragment. Sodium stearate and the monostearate esters of polyethylene glycol are examples of such molecules terminating in ionic and water-soluble fragments, respectively. Sodium stearate is more soluble in water than in oil while stearate esters of low molecular weight polyethylene glycols are more soluble in oil than water. Both types of surface-active agents are known to lower the surface tension at oil-water, water-air, and liquid-solid interfaces. It is this effect which accounts for the emulsifying, protecting and dispersing action of such materials. In addition it is known that to be effective, surface-active agents must also be capable of aggregating at low concentrations. Emulsions are possible only when aggregates (micelles) of molecules form at interfaces. Therefore, micelle formation at interfaces primarily accounts for surface and interfacial surface tension reduction.

The polyimides of the present invention include styrene-maleic anhydride copolymers having substantial amounts of anhydride residue, thus enhancing the effect of pendant amine-salts. Amine salts do not produce ash or residue on combustion, as in the case of alkali metal soaps; therefore the former are adaptable as "ashless" dispersants for engine oils. The instant polyimides also allow multipurpose additive preparation when, for example, some tertiary amine can be left unneutralized without adversely affecting surface activity but providing for neutralization of undesirable acid deposits formed in internal combustion engines. In this way, corrosion, lacquer, and sludge deposits in engines can be prevented or reduced. Additionally, the amine salts of this invention are powerful surface-active agents and possess water dissolving power (in oil) while not being water-soluble themselves. The additives, therefore, have utility in protecting "cold" engines from corrosion by water condensation on engine parts. An engine oil containing the additives of this invention can eliminate water as harmless vapor when the engine becomes hot.

It has now been discovered that oil-soluble, polymeric surface-active agents are obtained as polyimide-amine acid salts of styrene-maleic anhydride copolymers containing pendant tertiary amine groups neutralized to the extent of at least about 75 percent with sufficient monocarboxylic acid having an aliphatic carbon-to-carbon chain of at least about 8 carbon atoms, preferably as a terminal group, to give a mineral-oil soluble product. Thus the styrene-maleic anhydride copolymer is imidized to the extent of at least about 65 percent up to about 100 percent of its anhydride groups, with a dialkylaminoalkylamine neutralized to the extent of about 75 percent to 100 percent, with the long chain monocarboxylic acid. The styrene-maleic anhydride copolymer polyimide-amine acid salts can also contain imide groups or amide groups up to the extent of about 35 percent of its anhydride groups by reaction with a primary or secondary alkylamine, for instance, of about 8 to 30 carbon atoms.

The dialkylaminoalkylamines used in forming the polyimide-amine acid salts of this invention are of the formula

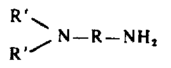

Where R is alkylene of 2 to about 30 carbon atoms, preferably 2 to about 5 carbon atoms, and R' is alkyl of 1 to about 5, preferably 1 to 2, carbon atoms. Examples of suitable dialkylaminoalkylamines are dimethylaminoethylamine, dimethylaminopropylamine, dimethylaminobutylamine, diethylaminopropylamine, diethylaminoamylamine, dipropylaminopropylamine, diamylaminoamylamine, dimethylaminooctadecylamine and dimethylaminoeicosylamine.

Mixed imide forms of the salts of this invention can be obtained by reacting primary alkylamines with a minor portion of the anhydride groups of the styrene-maleic anhydride copolymer. Similarly, mixed imide-amide forms of the salts of this invention can be obtained by reacting a minor portion of the copolymer anhydride groups with secondary dialkylamines. However the styrene-maleic anhydride copolymer should be imidated to the extent of at least about 65 percent of its anhydride groups with the dialkylaminoalkylamine and can contain up to about 35 percent imide groups or amide groups obtained by reaction, respectively, with the primary alkylamine or secondary dialkylamine. Preferably the styrene-maleic anhydride copolymer polymide salts contain little, if any, say up to about 5 percent or only up to about 2 percent, of carboxyl or ester groups. Such ester groups can result from reaction of the copolymer with an alkanol such as a lower alkanol, e.g., amyl alcohol.

The primary alkylamines which can be used to form imide groups in copolymer salts are of the formula $R-NH_2$ where R is alkyl of about 8 to 30 carbon atoms, preferably about 12 to 25 carbon atoms. A long chain is preferred to enhance the oil solubility of the products. Examples of suitable primary alkylamines are n-octylamine, decylamine, dodecylamine, octadecylamine, stearylamine, eicosylamine, docosylamine and pentacosylamine. The secondary alkylamines or dialkylamines which can be employed to form amide groups in the copolymer salts are of the formula $R-NHR'$, where R and R' are alkyl chains of about 8 to 30 carbon atoms, preferably about 12 to 25 carbon atoms, and often about 16 to 18 carbon atoms. Examples of such secondary amines are dioctylamine, didecylamine, didodecylamine, dioctadecylamine, distearylamine and dieicosylamine.

The ratio of styrene to maleic anhydride in the styrene-maleic anhydride copolymer of this invention should be in the range of about 0.1:1 to 5:1, preferably about 0.5:1 to 2:1, and most preferably about 1:1. The incorporation of more maleic anhydride affords more anhydride sites to convert to imides or amides. The styrene-maleic anhydride copolymer molecular weight can vary from about 400 to 5,000, preferably from about 1,000 to 5,000, and often is in the range of about 1,400 to 2,000. The higher molecular weight copolymers usually exhibit increased surface activity.

The monocarboxylic acids employed in this invention have an aliphatic carbon-to-carbon chain of at least 8 carbon atoms and often no more than about 36 total carbon atoms. Suitable carboxylic acids include monocarboxylic acids containing from about 12 to 22 carbon atoms, advantageously fatty acids, especially of about 16 to 22 carbon atoms. Straight carbon chained acids are preferred. Examples of suitable fatty acids include stearic acid, lauric acid, behenic acid, and the like. Examples of mono-olefinically, unsaturated or hydroxylated acids are oleic and hydroxystearic acid. The acid groups can be in presence of or part of an aromatic system, such as in dodecylbenzoic acid and phenylstearic acid.

The polyimide-amine salt is dissolved in the mineral oil composition in an effective amount to lower surface tension at oil-water, water-air, and liquid-solid interfaces, such as in the concentration range of about, for instance, less than about 1 percent, as low as about 0.006 percent, to about 100 percent, preferably about 1 to 2 to about 10 to 15 percent by weight based on the weight of the oil. The polyimide-amine salt thus dissolved in mineral oil formulations has the effect of an emulsifying, protecting and dispersing action. The polyimide-amine salt — mineral oil compositions can also contain water in solution or in emulsion up to about 80 percent or even up to about 100 percent or more by weight based on the weight of oil. Often in these formulations about 5 or 10 percent up to about 20 or 25 percent or more of water based on the weight of oil, can be dissolved or emulsified in the mineral oil with the polyimide-amine salt. It is understood that these compositions can contain other additives, e.g., antioxidants, etc.

The mineral oil of lubricating viscosity present in the products of this invention can have a viscosity, for instance, of about 50 to 2,000 SUS at 100°F, preferably about 70 to 500 SUS at 100°F. Good results have been obtained with acid-refined coastal oils having a viscosity of about 100 SUS at 100°F. Good results have also been obtained with Mid-continent neutral oils having a viscosity of about 150 SUS at 100°F. However, the mineral oil can also be a fuel oil or other mineral oil which is normally liquid.

Styrene and maleic anhydride can be polymerized to form polymers for use in this invention by various methods. Solution polymerization can be employed where the monomers are polymerized in a suitable solvent using as a polymerization aid a free-radical catalyst, such as a peroxide, preferably benzoyl peroxide, at a temperature of about 75° to 300°C. or more. Suitable solvents include the aromatic hydrocarbon solvents, such as cumene, p-cymene, xylene, toluene, etc. Other suitable solvents are the ketones, such as methylethylketone. A preferred manner of carrying out the polymerization is by what is known as incremental feed addition. By this method the monomers and catalyst are first dissolved in a portion of the solvent in which the polymerization is to be conducted and the resulting solution fed in increments into a reactor containing solvent heated to reaction temperature, usually the reflux temperature of the mixture.

When an aromatic solvent is employed as the solvent for the polymerization, the formation of the polymer causes a heterogeneous system, the polymer layer being the heavier layer and recoverable by merely decanting the upper aromatic solvent layer and drying. On the other hand when a ketone is the solvent, the formed copolymer is usually soluble in the solvent media so that recovery of the product necessitates a solvent-stripping operation.

The imides of this invention can be prepared by conventional methods, such as by simply heating at imide-forming temperature, the styrene-maleic anhydride copolymer with the amine. A temperature of about 125°C. is usually necessary to effect imide reaction and temperatures beyond about 250°C. are generally not utilized in that they may cause undesirable side reactions or degradation of the product. The preferred reaction temperature is from about 140° to 200°C. The reaction may be carried out in bulk but is preferably effected in the presence of a suitable mutual solvent for the reactants which may include, if desired, the mineral oil in which the reaction product is to be employed. Although the dialkylaminoalkylamine and primary or secondary alkylamine can be combined and reacted simultaneously with the styrene-maleic anhydride copolymer, one of these amines can be reacted with the copolymer before the other amine; thus the amines can be reacted in whole or in part in any desired order. Dropwise addition of the amine reactant is sometimes employed. The total reaction time can vary depending upon the particular reactants employed but will usually range from about 1 to 5 hours up to several days if necessary. The reaction can be carried out until the water of reaction ceases to distill from the mixture when imide formation is complete. When secondary alkylamines are employed amide formation results.

A preferred method of preparing the imides or mixed imides is to dissolve the styrene-maleic anhydride copolymer in amyl alcohol by heating to reflux temperature to get a half-ester- containing polymer. Then the dialkylaminoalkylamine and the primary or secondary alkylamine, if any, can be added and the heating continued at about 145°C. for about an hour. Vacuum can be applied, if necessary or desirable, to boil off amyl alcohol and water. If desired, xylene can be used as a solvent in admixture with the amyl alcohol and distilled off with the water. Partial neutralization of the tertiary amine group by at least about 75 percent to even substantially complete neutralization can be accomplished by merely mixing the carboxylic acid with the styrene-maleic anhydride copolymer imide - amine melt which can be at about room temperature or up to about 160°C.

The present invention will be further illustrated by the following specific examples.

EXAMPLE I

Imide Preparation

A mixture of 225 grams (the weight of one reoccurring copolymer unit) of a 1:1 styrene-maleic anhydride copolymer having a mol. wt. of about 1800; 88 grams of primary amyl alcohols (commercial mixture) and 80 g. of mixed xylene solvent (isomer mixture) was heated under reflux until clear (1–2 hours). To this, 102 grams (1 mole) of dimethylaminopropylamine is added in one portion. After stirring and heating for one hour, alcohol, xylene and water were distilled from the reaction vessel until the pot temperature reached 180°C. Sparging with nitrogen then removed traces of solvent. Table I gives data pertaining to imides made by this technique.

Amide-Imide Variation

By using primary alkyl amines such as octadecylamine, where alky imide forms, or secondary dialkyl amines, where amides result, the oil-solubility and hydrophobic-hydrophilic balance of the products can be modified. Table II has data concerning amide-imide made essentially by the procedure followed in producing the products of Table I.

EXAMPLE II

A mixture of 5.94 g (0.022 mole) octadecylamine and 2.32 grams (0.022 mole) dimethylamine propylamine in 6 ml. of xylene was added to 0.044 mole of a 1:1 styrene-maleic anhydride (having a mol. wt. of 1,800) amyl ester (as prepared in Example I). The mixture was reacted and freed of solvent as described in Example I.

EXAMPLE III

Amine Salt Preparation

A mixture of 2.73 g. of 31 percent octadecylimide: 69 percent dimethylaminopropyl (AS) imide of a 1:1 styrene-maleic anhydride copolymer (mol. wt. 1800) and 1.40 g. of stearic acid was heated to 150° C. with stirring until clear. The resulting product consists of 31 percent N-octadecylimide and 69 percent stearic acid salt of dimethylaminopropyl imide. Table III illustrates amine salt preparations of this type.

TABLE I

| Styrene-Maleic Anhydride Mole Ratio | Imide Resins Mol. Wt. | Reacting Equiv. Wt. | Wt. Dimethyl-amino Propylamine | M Moles of neutralizable amine per gram of product. |
|---|---|---|---|---|
| 1:1 | 1700–1900 | 225 | 102 | 3.2 |
| 2:1 | 1800–2000 | 306 | 102 | 2.6 |
| 3:1 | 1600–1800 | 410 | 102 | 2.0 |
| 1:1 | 400–600 | 250 | 102 | 3.3 |

TABLE II

| Reaction Amine Wt. (g) Mole. | Amide-Imide Variation[1] Composition Dimethylamino-Propylamine Wt. (g) | Mole. | Product Mol. % of Composition[3] | M Moles[2] (per gram)[4] |
|---|---|---|---|---|
| octadecylamine 5.94 0.022 | 2.32 | 0.022 | 50 "AS"[5] 50 $C_{18}$[6] | 1.25 |
| hydrogenated tallow secondary diamine 11.22 0.022 | 3.37 | 0.033 | 25 diamide[7] 75 "AS" | 1.51 |
| octadecylamine 3.96 0.015 | 3.04 | 0.030 | 66 "AS" 33 $C_{18}$ | 1.77 |
| octadecylamine 2.97 0.011 | 3.48 | 0.033 | 75 "AS" 25 $C_{18}$ | 2.1 |
| octadecylamine 8.91 0.033 | 1.16 | 0.011 | 25 "AS" 5 $C_{18}$ | 0.55 |

[1]1:1 styrene-maleic anhydride copolymer of 1800 molecular weight; 44 millimoles or 10.0 grams were used in reaction.
[2]Millimoles of neutralizable amine.
[3]Stoichiometry of product.
[4]Determines millimoles of fatty acid required for complete neutralization of amine.
[5]Fifty percent of all anhydride groups hold a pendant dialkylamino radical (AS).
[6]Designation for octadecylimide.
[7]Result of two secondary amine molecules reacting with one anhydride.

TABLE III

| Polyimide Composition AS(g) | octadecyl radical (of one mole) | Fatty Acid | Fatty Acid Degree Neutralization | Solubility and Surface Tension at Xylene/Water Interface Solubility[1] | Du Nuoy Readings[2] at 0.03% Concentration | Du Nucy Readings at 0.006% Concentration |
|---|---|---|---|---|---|---|
| 100% | 0% | Stearic[3] acid | complete | naphthenic[4] oil | 3 | 4 |
| 100% | 0% | " | 75% | " | 10.5 | 13.5 |
| 50% | 50% | " | complete | cyclo-[5] paraffinic oil | 13.1 | 20.7 |
| 25% | 75% | " | complete | " | 11.6 | 15.5 |
| 66% | 33% | " | complete | naphthenic oil[4] | 11.7 | 15.6 |
| 75% | 25% | " | complete | naphthenic oil[4] | — | — |

TABLE III-continued

| Polyimide Composition AS(g) | octadecyl radical (of one mole) | Fatty Acid | Fatty Acid Degree Neutralization | Solubility and Surface Tension at Xylene/Water Interface Solubility[1] | Du Nuoy Readings[2] at 0.03% Concentration | Du Nucy Readings at 0.006% Concentration |
|---|---|---|---|---|---|---|
| 25% | 75% | — | none | low aromatic oil[7] | — | 21.0 |
| 100% | 0% | Lauric[6] acid | complete | naphthenic oil[4] | at 0.036% Conc. 3.0 | 10.5 |
| 100% | 0% | Benehic[8] acid | complete | naphthenic oil[4] | 10.5 | 12.8 |
| Untreated xylene/water interface | | | | | 34-5 | |

[1]Solubility of product was determined by heating 5 parts of solid with 95 parts oil; if upon cooling no solid separated the product was deemed soluble.
[2]Du Nuoy balance is a torsion balance for measuring force necessary to lift a platinum ring from surface or interface of liquids. The greater the Du Nuoy reading, the greater the surface tension at the interface. Conversely, lower readings exemplify good surface acitvity in an additive, especially at low concentrations.
[3]Stearic acid-"triple pressed", almost equal parts mixture or stearic ($C_{18}$) and palmitic ($C_{16}$) acids.
[4]High aromatic-containing No. 2 fuel oil.
[5]Nearly complete hydrogenated aromatic lubricating oil.
[6]91% $C_{12}$ acid.
[7]Mid-Continent lubricating oil.
[8]91% $C_{22}$ acid.

EXAMPLE IV

To 0.044 mole of heated amyl ester of a 1:1 styrene-maleic anhydride copolymer (mol. wt. 1800), a mixture of 11.22 grams (0.022 mole) of hydrogenated tallow secondary diamine (mol. wt. 510) and 3.37 grams of dimethylaminopropylamine in 10 ml. of xylene was added with stirring. After heating and distilling the solvent the molten residue was poured into a pan and allowed to solidify. One gram of product contains 1.51 m moles of AS which would therefore require 1.51 m moles of stearic acid for complete neutralization. The preparation of Example IV is illustrated in Table IV.

TABLE IV

| Polyimide Composition | Amine-Salts of Stearic Acid (Diamide Composition) Solubility | Du Nuoy Readings at 0.03% | Du Nuoy Readings at 0.006% |
|---|---|---|---|
| 75% "AS" 25% hydrogenated[1] tallow secondary diamine | xylene | 10.5 | 15.2 |

[1]hydrogenated "fat" acids, converted to . Two of these units are required per anhydride.

Table V shows solubility test in xylene of the dimethylaminopropylimide prepared as in Example I with a copolymer with a 3:1 motor ratio of styrene-maleic anhydride having a molecular weight of 1,800 which has been completely neutralized with stearic acid.

TABLE V

| Polyimide Composition | Fatty Acid Degree of Neutralization | Surface Tension "AS" - Amine-Salts Solubility | Du Nuoy Readings at 0.03% | Du Nuoy Readings at 0.006% |
|---|---|---|---|---|
| 100% "AS" | stearic acid complete | xylene | 15.0 | 18.0 |

EXAMPLE V

The results in Table VI below illustrate another utility for the imide-amine salts of this invention. Oil is not known to dissolve much more than a few hundredths of percent of water. By using these salts as additives, metal surfaces as found in engines and power trains can be protected from water by keeping the latter in solution and thus preventing its condensation on surfaces. The amine salts can hold, for instance, thirty to seventy molecules of water per polar radical. Again, this behavior is probably due to the relative ease of "micelle" formation and the fact that they consist of appropriately placed "voids" capable of holding larger numbers of water molecules. Non-inflammable "hydraulic" fluids, less fire susceptible jet fuels, and electrolyte containing oils can be prepared by incorporating thereon the imide-amine salts of this invention. The latter application is useful where fluxing materials or inhibitors are needed to prevent corrosion by contaminants in oil.

TABLE VI

| Polyimide Composition | Fatty Acid | Water Dissolving Power of 100% Neutralized "AS" Imide-Amide Salts of Example I Additive Conc. | Oil | Water Dissolved[1] on Weight of Oil |
|---|---|---|---|---|
| 100% "AS" | stearic acid | 10% | No.2 fuel oil | 8% |
| 100% "AS" | lauric acid | 10% | " | 0% |

TABLE VI-continued

| Water Dissolving Power of 100% Neutralized "AS" Imide-Amide Salts of Example I | | | | |
|---|---|---|---|---|
| Polyimide Composition | Fatty Acid | Additive Conc. | Oil | Water Dissolved[(1)] on Weight of Oil |
| 100% "AS" | behenic acid (60% pure) | 10% | " | 21% |
| 100% "AS" | behenic acid (91% pure) | 10% | " | 0% |

[(1)]as clear solution

EXAMPLE VI

Wear data on additives as lubricating oil modifiers.

The following data was obtained in the Shell 4-ball test with 5 percent concentration of the imides in petroleum lubricating oil having a viscosity of about 200 SUS at about 100°F. and having a 95 V.I. The test was run at 130°F. at 600 and 1,800 rpm and at 180°F. at 600 and 1,800 rpm with a load of 40 Kg.

TABLE VII

| | Wear Scar (mm.) | | | |
|---|---|---|---|---|
| | At 130°F. | | At 180°F. | |
| Imide | 600 rpm | 1800 rpm | 600 rpm | 1800 rpm |
| No additive | 0.603 | 0.633 | 0.60 | 1.997 |
| 100% $C_{18}$ imide of styrene-maleic anhydride having a 1:1 mole ratio of styrene to maleic anhydride, and a molecular weight of 1800 | 0.60 | 0.627 | 0.546 | 1.917 |
| 50:50 "mixed" imide $C_{18}$ plus dimethylamino propylamine 100% stearate salt of styrene maleic anhydride having a 1:1 mole ratio of styrene to maleic anhydride and having a molecular weight of 1800. | 0.39 | 0.438 | 0.52 | 0.545 |

The results clearly show that a lower scar diameter, or less wear, is obtained when the salts of this invention are present in the lubricating oil.

EXAMPLE VII

A 5 to 10 percent concentration of the 50—50 mixed imide $C_{18}$ plus dimethylaminopropylamine stearate salt of styrene-maleic anhydride of Example VI in a petroleum lubricating oil having a viscosity of about 200 SUS at about 100°F and having a 95 V.I. gave 4 to 6 weeks emulsion stability at 25, 50 and 80 percent (by weight of the total emulsion) water levels. These emulsions were made by adding water to a warm additive-oil solution in a Waring blender. The time it took for 1 to 2 percent of the emulsion to separate into a clear top layer determined stability.

It is claimed:

1. Polyamide amine salts of a styrene-maleic anhydride copolymer; said styrene-maleic anhydride copolymer consisting essentially of a molar ratio of polymerized styrene to polymerized maleic anhydride of 0.1:1 to 5:1 and having an average molecular weight of 400 to 5,000, and said copolymer being imidized to the extent of at least 65 per cent of its anhydride groups with a dialkylaminoalkylamine containing tertiary amine groups of the formula

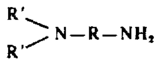

wherein R is alkylene of 2 to 30 carbon atoms and R' is alkyl of 1 to 5 carbon atoms, and wherein the tertiary amine groups of said dialkylaminoalkylamine are at least 75 per cent neutralized with a monocarboxylic acid having an aliphatic carbon to carbon chain of 8 to 36 carbon atoms.

2. The product of claim 1 wherein the styrene-maleic anhydride copolymer is further imidated up to 35 percent with a long chain alkyl-primary amine.

3. The product of claim 2 wherein the alkyl-primary amine is octadecylamine.

4. The product of claim 1 wherein the styrene-maleic anhydride copolymer is amidated to the extent of 35 percent with a dialky-secondary amine.

5. The product of claim 4 wherein the dialky-secondary amine is hydrogenated tallow secondary diamine.

6. The product of claim 1 wherein the monocarboxylic acid is stearic acid.

7. The product of claim 1 wherein the monocarboxylic acid is lauric acid.

8. The product of claim 1 wherein the monocarboxylic acid is behenic acid.

9. The salts of claim 1 wherein the dialkylaminoalkylamine is dimethylamine propylamine and the monocarboxylic acid is stearic acid.

* * * * *